United States Patent
Kim et al.

(10) Patent No.: US 10,271,984 B2
(45) Date of Patent: Apr. 30, 2019

(54) SHOCK ABSORBING DEVICE USING DAMPER FOR ANKLE AND KNEE JOINTS

(71) Applicant: Soongsil University Research Consortium Techno-Park, Seoul (KR)

(72) Inventors: Jin Oh Kim, Seoul (KR); Jeong Gil Hwang, Seoul (KR)

(73) Assignee: SOONGSIL UNIVERSITY RESEARCH CONSORTIUM TECHNO-PARK, Seoul (KR)

( * ) Notice: Subject to any disclaimer, the term of this patent is extended or adjusted under 35 U.S.C. 154(b) by 361 days.

(21) Appl. No.: 15/231,882

(22) Filed: Aug. 9, 2016

(65) Prior Publication Data

US 2017/0042716 A1    Feb. 16, 2017

(30) Foreign Application Priority Data

Aug. 10, 2015   (KR) .................. 10-2015-0112450

(51) Int. Cl.
| | |
|---|---|
| *A43B 3/16* | (2006.01) |
| *A43B 7/20* | (2006.01) |
| *A43B 7/24* | (2006.01) |
| *A61F 5/01* | (2006.01) |

(52) U.S. Cl.
CPC ............ *A61F 5/0195* (2013.01); *A43B 3/163* (2013.01); *A43B 7/20* (2013.01); *A61F 5/0106* (2013.01); *A61F 5/0118* (2013.01); *A43B 7/24* (2013.01)

(58) Field of Classification Search
CPC .. A61F 2/64; A61F 2/66; A61F 2/6607; A61F 5/0195; A61F 5/0111; A61F 5/0113; A61F 5/0127; A43B 7/20; A43B 7/147; A43B 7/32; A61H 1/0237; A61H 1/024; A61H 1/0262; A61H 1/0266; A61H 3/00; A61H 2003/001; A61H 2003/005
See application file for complete search history.

(56) References Cited

U.S. PATENT DOCUMENTS

| | | | |
|---|---|---|---|
| 2006/0069448 A1* | 3/2006 | Yasui .................. | A61F 2/60 623/24 |
| 2013/0173022 A1* | 7/2013 | Arabian ............... | A61F 2/6607 623/49 |
| 2015/0127117 A1 | 5/2015 | Herr | |

FOREIGN PATENT DOCUMENTS

| | | |
|---|---|---|
| JP | 2002-021912 A | 1/2002 |
| KR | 10-0688327 B1 | 3/2007 |
| KR | 10-1056621 B1 | 8/2011 |

* cited by examiner

*Primary Examiner* — Kari K Rodriquez
(74) *Attorney, Agent, or Firm* — Pearne & Gordon LLP

(57) ABSTRACT

The shock absorbing device for ankle and knee joints may include a shoe part; a weight dispersing pad part configured to accommodate a user's leg inserted therein; a piston unit including a plurality of pistons respectively connected to upper portions of the shoe part in a vertical direction and configured to be moved upwards and downwards; and a damper part connected between the piston unit and the weight dispersing pad part, wherein the damper part has an annular shape so as to be connected to the weight dispersing pad part along the circumference of the weight dispersing pad part, the pistons are inserted into an internal space of the damper part, and the damper part performs a damping operation through oil stored in the internal space of the damper part according to the upward/downward movement of the piston.

5 Claims, 4 Drawing Sheets

PISTON INSERTION HOLES

PISTON INSERTION HOLES

SHOCK ABSORBING DEVICE USING DAMPER FOR ANKLE AND KNEE JOINTS

CROSS-REFERENCE TO RELATED APPLICATION

This application claims the benefit of Korean Patent Application No. 10-2015-0112450 filed on Aug. 10, 2015, the entire disclosures of which are incorporated herein by reference.

BACKGROUND

The various embodiments described herein pertain generally to a shock absorbing device using a damper for ankle and knee joints.

In general, patients with degenerative arthritis or the elderly with weak knees may use shock absorbing devices for joints to protect their knees in a safe manner and to reduce fatigue and external impact on the knee joints. These shock absorbing devices are designed to use a typical controllable method for the purposes of controlling and stabilizing lateral movement of the knee joints, delimiting or correcting bending of the knee joints, and preventing the recurrence of injury of the knee joints.

Conventional methods for protecting a joint include: a method of wrapping the entire joint with an elastic body or wrapping dampers on the left and right sides of the joint with an elastic body, a method of strapping the body part to a brace, and so forth. The conventional dampers and the elastic bodies, however, have drawbacks in that they may not react to a distortion of the joint in a forward-backward direction though they react to a distortion of the joint in a left-right direction. Further, in case of wrapping the entire joint with the elastic body, the joint may not be rotated. Furthermore, in case of using the brace, although a shock or impact from the ground may not be delivered to the joint portion, it may be delivered upwards to another body portion.

In this regard, Korean Patent No. 1056621 (entitled "Knee brace and attachable ankle brace") discloses a method of protecting a knee by fixing one's lower body to braces.

Further, Korean Patent No. 0688327 (entitled "Orthopedic knee joint brace) describes a technique of absorbing a shock by using a pair of left and right damping pivot assemblies.

BRIEF SUMMARY

In view of the foregoing, exemplary embodiments provide a shock absorbing device for ankle and knee joints, including a weight dispersing pad part formed to accommodate a user's leg inserted therein, a piston unit including a plurality of pistons respectively connected to upper portions of a shoe part in a vertical direction and configured to be moved up and down, and a damper part connected between the piston unit and the weight dispersing pad part.

However, the problems sought to be solved by the present disclosure are not limited to the above description.

In accordance with an exemplary embodiment of the present disclosure, a shock absorbing device for ankle and knee joints may include a shoe part; a weight dispersing pad part configured to accommodate a user's leg inserted therein; a piston unit including a plurality of pistons respectively connected to upper portions of the shoe part in a vertical direction and configured to be moved upwards and downwards; and a damper part connected between the piston unit and the weight dispersing pad part, wherein the damper part has an annular shape so as to be connected to the weight dispersing pad part along the circumference of the weight dispersing pad part, the pistons are inserted into an internal space of the damper part, and the damper part performs a damping operation through oil stored in the internal space of the damper part according to the upward/downward movement of the piston.

According to the shock absorbing device for angle and knee joints of the exemplary embodiment, resistance is not generated to a normal movement of the joints such as rotation but may be generated to an abnormal movement such as constriction, extension, distortion and vibration. Thus, the ankle joint can be protected, and a force (impact) applied to other joints such as the knee joint can be reduced.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
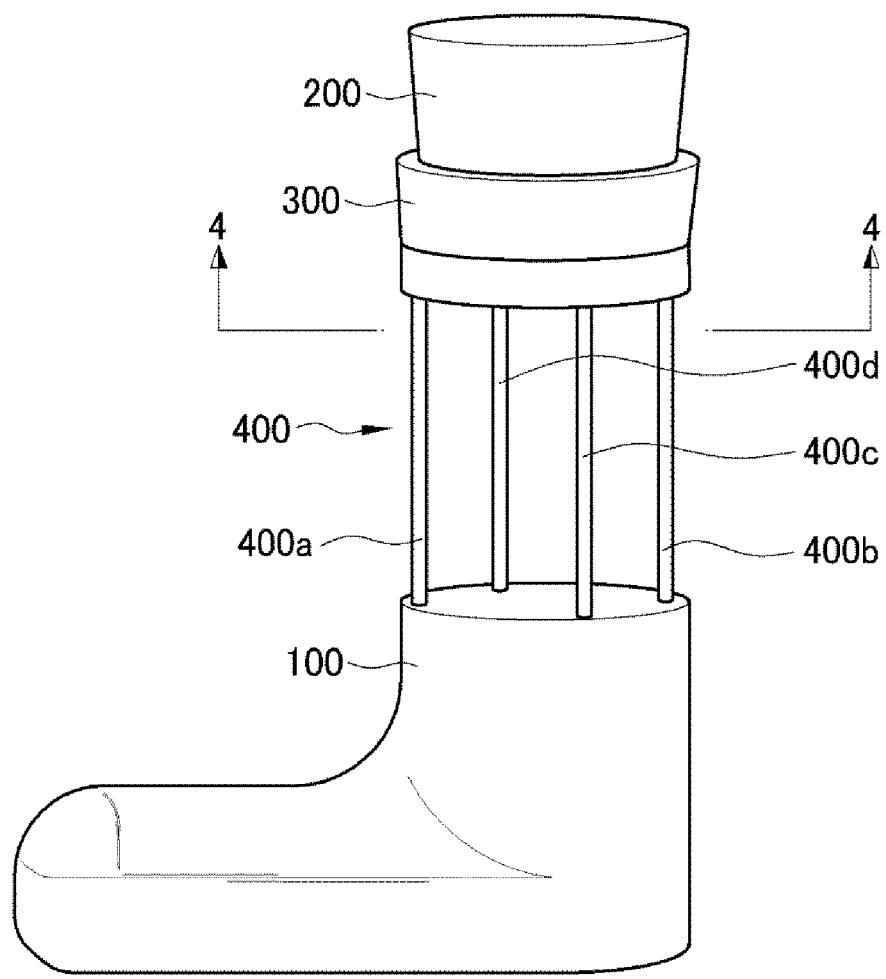
FIG. 1 is a diagram illustrating an example of a shock absorbing device for ankle and knee joints according to an exemplary embodiment.

Hereinafter, exemplary embodiments will be described in detail with reference to the accompanying drawings so that the inventive concepts may be readily implemented by those skilled in the art. However, it is to be noted that the present disclosure is not limited to the exemplary embodiments but can be realized in various other ways. In the drawings, certain parts not directly relevant to the description are omitted to enhance the clarity of the drawings, and like reference numerals denote like parts throughout the whole document.

Throughout the document, the terms "connected to" or "coupled to" are used to designate a connection or coupling of one element to another element and include both a case where an element is "directly connected or coupled to" another element and a case where an element is "electronically connected or coupled to" another element via still another element. Further, throughout the document, the term "comprises or includes" and/or "comprising or including" used in the document means that one or more other components, steps, operations, and/or the existence or addition of elements are not excluded in addition to the described components, steps, operations and/or elements.

Figure 2A:
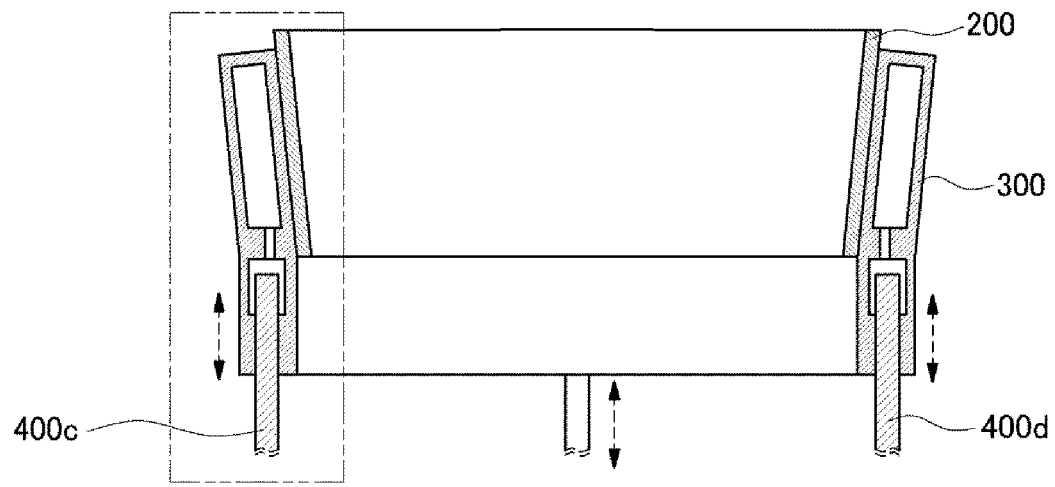
FIG. 2A is a diagram illustrating a damper part of the shock absorbing device for ankle and knee joints according to the exemplary embodiment.
Figure 2B:
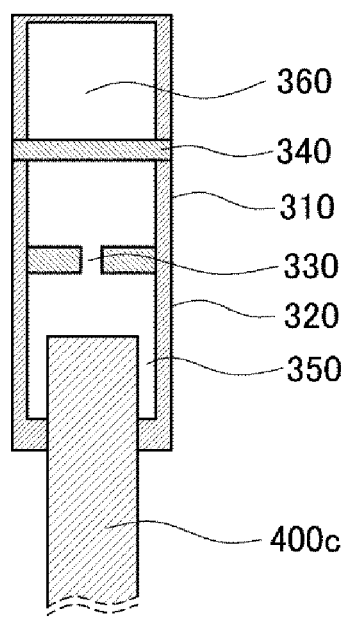
FIG. 2B is an enlarged view of a portion of the damper part shown in FIG. 2A.

FIG. 1 is a diagram illustrating an example of a shock absorbing device for ankle and knee joints, according to an exemplary embodiment. FIGS. 2A and 2B are diagrams illustrating a damper part of the shock absorbing device for ankle and knee joints according to the exemplary embodiment.

Here, the shock absorbing device for ankle and knee joints using the damper will be elaborated.

Referring to FIG. 1, the shock absorbing device using the damper includes a shoe part 100, a weight dispersing pad part 200, a damper part 300 and a piston unit 400.

The shoe part 100 may be put on a user's foot.

The weight dispersing pad part 200 may be formed to accommodate a user's leg inserted therein.

The piston unit 400 includes a multiple number of pistons 400a, 400b, 400c, 400d respectively connected to top portions of the shoe part 100 in a vertical direction and configured to be movable up and down.

The damper part 300 has an annular shape so as to be connected to the weight dispersing pad part 200 along the circumference thereof. The piston unit 400 is inserted into an internal space of the damper part 300. The damper part 300 is capable of performing a damping operation through oil 350 stored in the internal space of the damping unit 300 as the piston unit 400 is moved up and down.

The weight dispersing pad part 200 may be formed to be connected to the annular damper part 300 along the inner circumference thereof and is made of a material having elasticity. The weight dispersing pad part 200 is configured to deliver a force to the entire leg by dispersing the force through the damper part 300. Thus, the weight intensively applied to the joints can be reduced.

The piston unit 400 includes, for example, four pistons 400a, 400b, 400c, 400d. These pistons 400a-d are arranged along the upper circumference of the shoe part 100 and along the lower circumference of the damper part 300 at a regular interval therebetween. The number of the pistons of the piston unit 400 is nothing more than an example and is not limited to the above example.

That is, as the pistons 400a-d of the piston unit 400 are arranged around the leg of the user at a regular distance therebetween, resistance to rotary motion of the joints can be minimized.

Furthermore, a front piston 400a and a rear piston 400b of the piston unit 400 can be arranged to correspond to a displacement caused by a rotary motion of the joint. Here, the front piston 400a and the rear piston 400b of the piston unit 400 may be formed to have different thicknesses, so that the resistance to the rotary motion of the joint can be minimized.

Now, a shape and an operational principle of the damper part 300 according to the exemplary embodiment will be explained in detail.

Referring to FIGS. 2A and 2B, the damper part 300 includes an upper space 310, a lower space 320 and a hole 330 connecting the upper space 310 and the lower space 320.

The hole 330 is located at a midway position between the upper space 310 and the lower space 320 and allows the upper space 310 and the lower space 320 to communicate with each other.

The cross sectional area of the hole 330 is smaller than the cross sectional areas of the upper space 310 and the lower space 320. The movement of oil 350 through the hole 330 helps the damping operation of the damper part 300.

As the pistons 400a-d of the piston unit 400 is inserted into the lower space 320 and moved vertically, the oil 350 accommodated in the lower space 320 is moved into the upper space 310 through the hole 330. Through this process, the damping operation is performed.

The piston unit 400 is inserted into a part of the lower space 320, and the remaining portion of the lower space 320 may be filled with the oil 350.

The hole 330 of the damper part 300 allows the oil 350, which is moved into the upper space 310 as the piston unit 400 is moved upwards, to pass therethrough.

As the width of the hole 330 gets smaller and the length of the hole 330 gets longer, resistance generated when the oil 350 accommodated in the lower space 320 is moved into the upper space 310 may be increased.

A partition 340 may be disposed in the upper space 310 of the damper part 300 to be located on the surface of the oil 350. The partition 340 may be provided within the upper space 310 as an individual part and is configured to be movable up and down within the upper space 310.

Above the partition 340 which is installed in the upper space 310 is stored a gas 360, and under the partition 340 is stored the oil 350.

Since both lateral sides of the partition 340 are shrink-fit into the upper space 310, the partition 340 can be moved up and when a pressure of the oil 350 is applied thereto.

Due to the presence of the partition 340 provided in the upper space 310 of the damper part 300, resistance to the flow of the oil 350 is generated when the oil 350 in the lower space 320 is moved into the upper space 310.

By way of example, when the piston unit 400 inserted into the lower space 320 of the damper part 300 is moved upwards, the room within the lower space 320 is reduced, so that the oil 350 stored in the lower space 320 is moved into the upper space 310 through the hole 330. During this movement of the oil 350, primary resistance is generated when the oil 350 passes through the hole 330 which connects the upper space 310 and the lower space 320. Further, during the movement of the oil 350, secondary resistance is generated when the oil 350 pushes the partition 340 in the upper space 310 upwards toward the portion where the gas 360 is stored.

Thus, the damper part 300 having such resistances can protect the joints from abnormal constriction, extension, distortion and vibration.

Figure 3A:
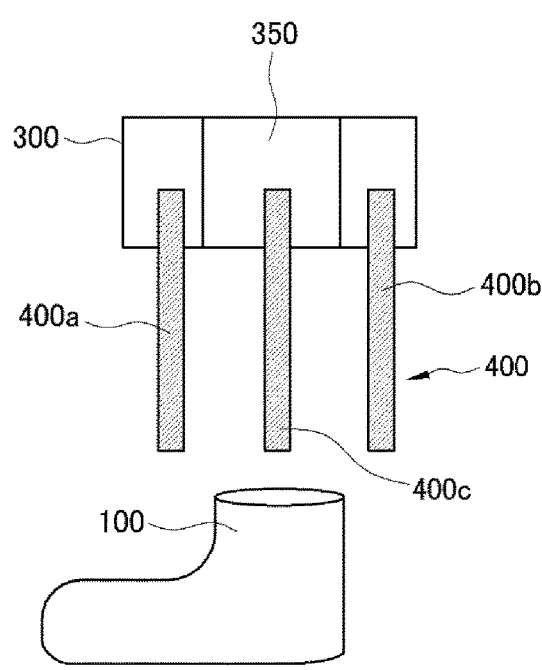
FIG. 3A is a diagram illustrating a movement of pistons of a piston unit according to a movement of the shock absorbing device for ankle and knee joints of the exemplary embodiment showing the shock absorbing device generally aligned with a horizontal plane.
Figure 3B:
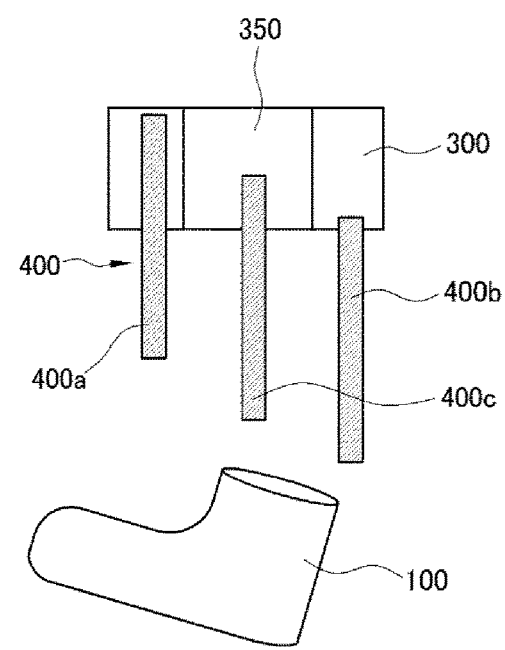
FIG. 3B is a diagram illustrating a movement of pistons of a piston unit according to a movement of the shock absorbing device for ankle and knee joints of the exemplary embodiment showing the shock absorbing device generally skewed or angled with respect to the horizontal plane.

FIGS. 3A and 3B are diagrams for describing a movement of the piston unit 400 according to a damping operation of the shock absorbing device for ankle and knee joints in accordance with the exemplary embodiment.

Referring to FIGS. 3A and 3B, if the user stops walking, the ends of the pistons 400a-d of the piston unit 400 are aligned along a horizon plane. If the user walks, a front piston 400a located at the front side of the shoe part 100 is moved upwards from the horizon plane, whereas a rear piston 400b located at the rear side of the shoe part 100 is moved downwards from the horizon plane. At this time, since the oil 350 stored in the damper part 300 flows in an amount corresponding to the movement of the pistons 400a, 400b of the piston unit 400, the volume of the oil 350 can be maintained.

By way of non-limiting example, when the user stops walking, the ends of the pistons 400a-d of the piston unit 400 inserted in the damper part 300 are aligned along the horizon plane, and the oil 350 stored in the damper part 300 may also be evenly distributed along the horizon plane.

If the shoe part 100 is taken off the ground when the user walks, the front side of the shoe part 100 is moved upwards. As the front side of the shoe part 100 is moved upwards, the front piston 400a of the piston unit 400 connected to the damper part 300 to correspond to the front side of the shoe part 100 is moved into the upper space 310 of the damper part 300 from the lower space 320 thereof. Further, as the rear side of the shoe part 100 is moved downwards, the rear piston 400b of the piston unit 400 connected to the damper part 300 to correspond to the rear side of the shoe part 100 is moved into the lower space 320 of the damper part 300 from the upper space 310 thereof. Further, as the left side or the right side of the shoe part 100 is moved upwards, a left piston 400c or a right piston 400d of the piston unit 400 connected to the damper part 300 to correspond to the left side or the right side of the shoe part 100 is moved into the upper space 310 of the damper part 300 from the lower space 320 thereof.

Furthermore, if the user steps on the ground with the shoe part 100 to walk, the front side of the shoe part 100 is moved downwards. As the front side of the shoe part 100 is moved downwards, the front piston 400a of the piston unit 400 connected to the damper part 300 to correspond to the front side of the shoe part 100 is moved into the lower space 320 of the damper part 300 from the upper space 310 thereof. Further, as the rear side of the shoe part 100 is moved upwards, the rear piston 400b of the piston unit 400 connected to the damper part 300 to correspond to the rear side of the shoe part 100 is moved into the upper space 310 of the damper part 300 from the lower space 320 thereof. Further, as the left side or the right side of the shoe part 100 is moved downwards, the left piston 400c or the right piston 400d connected to the damper part 300 to correspond to the left side or the right side shoe part 100 is moved into the lower space 320 of the damper part 300 from the upper space 310 thereof.

That is, the oil 350 corresponding to the space filled with the upwardly moved piston 400b of the piston unit 400 may be moved into the space from which the downwardly moved piston 400a of the piston unit 400 is removed.

Thus, in the shock absorbing device for ankle and knee joints including the damper part 300, resistance may be generated to an abnormal movement such as constriction, extension, distortion and vibration without generating resistance to a normal movement of the joints such as rotation. Thus, the joints can be protected.

Figure 4A:
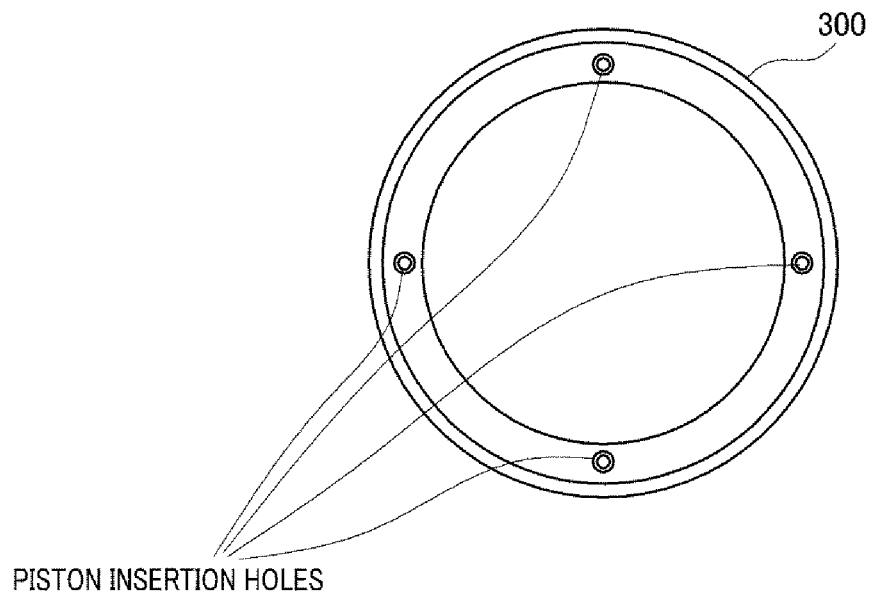
FIG. 4A is a cross sectional diagram taken along line 4-4 in FIG. 1 illustrating the damper part of the shock absorbing device for ankle and knee joints according to the exemplary embodiment.
Figure 4B:
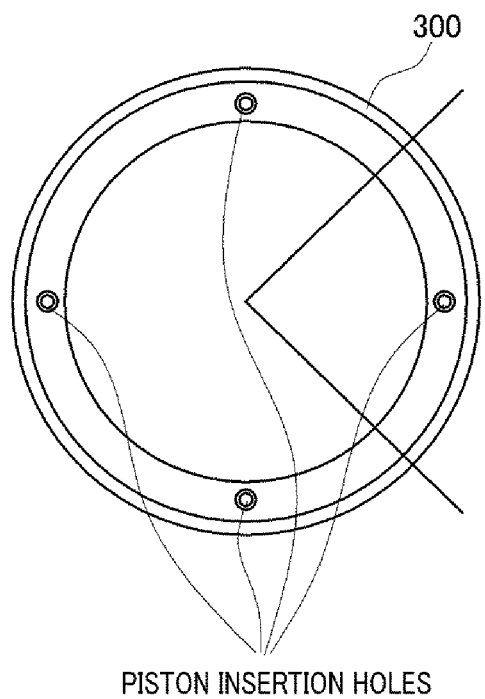
FIG. 4B is a cross sectional diagram illustrating the damper part of the shock absorbing device for ankle and knee joints partially sectioned according to the exemplary embodiment.

FIGS. 4A and 4B are cross sectional diagrams illustrating the damper part of the shock absorbing device for ankle and knee joints according to the exemplary embodiment.

As depicted in FIGS. 4A and 4B, piston insertion holes for allowing the pistons 400a-d of the piston unit 400 to be inserted therein may be provided at the lower end of the damper part 300 having the annular shape. Further, either the left side or the right side of the damper part 300 may be two separable parts forming ¾ and ¼ of a circle, respectively, as illustrated by the lines in FIG. 4B. The damper part 300 having this structure can improve convenience of the user who wears the shock absorbing device.

The above description of the illustrative embodiments is provided for the purpose of illustration, and it would be understood by those skilled in the art that various changes and modifications may be made without changing technical conception and essential features of the illustrative embodiments. Thus, it is clear that the above-described illustrative embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the illustrative embodiments. It shall be understood that all modifications and embodiments conceived from the meaning and scope of the claims and their equivalents are included in the scope of the inventive concept.

We claim:

1. A shock absorbing device for ankle and knee joints, comprising:
    a shoe part configured to be put on a user's foot;
    a weight dispersing pad part configured to accommodate a user's leg inserted therein and made of a material having elasticity;
    a piston unit including a plurality of pistons respectively connected to upper portions of the shoe part in a vertical direction and configured to be moved upwards and downwards; and
    a damper part connected between the piston unit and the weight dispersing pad part,
    wherein the damper part has an annular shape so as to be connected to the weight dispersing pad part along the circumference of the weight dispersing pad part,
    the pistons are inserted into an internal space of the damper part, and
    the damper part performs a damping operation through oil stored in the internal space of the damper part by upward and downward movement of the pistons,
    a number of the plurality of pistons of the piston unit is four, and the four pistons are arranged along an upper circumference of the shoe part and along a lower circumference of the damper part at a regular distance therebetween.

2. The shock absorbing device of claim 1,
    wherein the damper part comprises an upper space, a lower space and a hole connecting the upper space and the lower space, and
    the pistons of the piston unit are inserted into the lower space, and the damping operation is performed when the oil stored in the lower space is moved into the upper space through the hole by upward and downward movement of the pistons of the piston unit.

3. The shock absorbing device of claim 2,
    wherein a partition is disposed in the upper space of the damper part to be located on the surface of the oil.

4. The shock absorbing device of claim 1,
    wherein when a user stops walking, ends of the pistons of the piston unit are aligned along a horizon plane,
    when the user walks, a piston located at a front side of the shoe part is moved upwards relative to the horizon plane, a piston located at a rear side of the shoe is moved downwards relative to the horizon plane, and a volume of the oil is maintained as the oil stored in the damper part flows in an amount corresponding to the movement of the pistons of the piston unit.

5. A shock absorbing device for ankle and knee joints, comprising:
a shoe part configured to be put on a user's foot;
a weight dispersing pad part configured to accommodate a user's leg inserted therein;
a piston unit including a plurality of pistons respectively connected to upper portions of the shoe part in a vertical direction and configured to be moved upwards and downwards; and
a damper part connected between the piston unit and the weight dispersing pad part,
wherein the damper part has an annular shape so as to be connected to the weight dispersing pad part along the circumference of the weight dispersing pad part,
the pistons are inserted into an internal space of the damper part, and
the damper part performs a damping operation through oil stored in the internal space of the damper part by upward and downward movement of the pistons.

* * * * *